United States Patent [19]

Laboureau et al.

[11] Patent Number: 4,848,328
[45] Date of Patent: Jul. 18, 1989

[54] AGRAFFE FOR OSTEOSYNTHESIS

[76] Inventors: Jacques P. Laboureau, Rue Fontaine Billenois; Georges Comte, 19, rue Colson, both of 21000 Dijon, France

[21] Appl. No.: 189,427

[22] Filed: May 2, 1988

Related U.S. Application Data

[63] Continuation-in-part of Ser. No. 865,155, May 20, 1986, abandoned.

[51] Int. Cl.⁴ .............................................. A61F 5/04
[52] U.S. Cl. ............................................. 128/92 YC
[58] Field of Search ... 128/92 YC, 92 YD, 334 R:334 C; 411/457

[56] References Cited

U.S. PATENT DOCUMENTS

| | | | |
|---|---|---|---|
| 1,412,582 | 4/1922 | Vaile | 411/457 |
| 4,263,904 | 4/1981 | Judet | 128/92 YC |
| 4,278,091 | 7/1981 | Borzone | 128/92 YC |
| 4,414,967 | 11/1983 | Shapiro | 128/92 YC |
| 4,454,875 | 7/1984 | Pratt et al. | 128/92 YC |
| 4,570,623 | 2/1986 | Ellison et al. | 128/92 YC |

OTHER PUBLICATIONS

Zimmer Product Catalogue, 1978, p. B14, Epiphyseal Staples.

Primary Examiner—John D. Yasko
Attorney, Agent, or Firm—McAulay, Fields, Fisher, Goldstein & Nissen

[57] ABSTRACT

An agraffe or staple-shaped element for osteosynthesis intended for fixing the focus of an osteotomy while awaiting consolidation of web from which issue two lateral arms having pointed ends adapted to penetrate in the bone. The web of the agraffe comprises two parts inclined with respect to each other and forming an outwardly open obtuse angle. Each of the lateral arms of the agraffe presents, near its zone of join with the web, fins projecting from the front faces of this arms, such fins reinforcing the anchoring of the agraffe in the zone.

20 Claims, 3 Drawing Sheets

AGRAFFE FOR OSTEOSYNTHESIS

This application is a continuation-in-Part of application Ser. No. 865,155 filed on May 20, 1986 now abandoned.

BACKGROUND OF THE INVENTION

1. Field of the Invention

The present invention relates to an agraffe for osteosynthesis. More particularly, the invention is intended for fixing the focus of an osteotomy while awaiting consolidation of the bone.

2. Description of the Prior Art

Agraffes or a staple-shaped element for osteosynthesis are already known which are generally in the form of a U-shape with two lateral arms perpendicular to a central web. Certain agraffes present lateral arms which are parallel, but inclined with respect to the web by an angle different from 90°. Other known agraffes, generally in the form of a U-shape, present, in one angle, a step constituting a re-entering angle at 90°, with the result that the lateral arm issuing from this step is shorter than the opposite lateral arm. This latter agraffe, which is used for holding the two parts of a tibia sawn beneath the tibial plateau, presents a drawback of not being perfectly adapted to the particular shape of the head of the tibia for this zone. Furthermore, not all presently known agraffes for osteosynthesis ensure a perfect anchoring of the agraffe and consequently a good holding of the two parts of the bone during consolidation thereof.

Prior art also known from the prosecution of application Ser. No. 865,155 and contained therein is Zimmer Product Catalogue 1978, page B14, Epiphyseal Staples, 128/92YC; U.S. Pat. Nos. 4,454,875 to Pratt et al, 4,278,091 to Borzone, 4,414,967 to Shapiro, 4,263,904 to Judet, 4,570,623 to Ellison et al., 1,412,582 to Vaile, 3,618,447 to Goins, 4,014,492 to Rothfuss, 2,142,782 to Gillette, 4,263,903 to Griggs; Swiss Patent No. 597,838 to National Research Development Corporation; French Patent No. 2,248,435 to Illinois Tool Works; and United Kingdom Patent No. 2,118,662 to Techmedica, Inc.

SUMMARY OF THE INVENTION

It is an object of the present invention to overcome these drawbacks by providing an "agraffe for osteosynthesis" of particularly simple design, perfectly adapted to the outer profile of the bone and ensuring a very firm anchoring in the hard outer part of the bone.

A further object of the invention is to provide at least one side and preferably both sides of each leg with a fin to provide for increased contact surface between the staple and the bone.

Another object of the invention is to provide fins which are preferably bevel-shaped and have a triangular cross-section in order to provide for increased contact surface between the staple legs and the cortical bone.

To this end, this agraffe for osteosynthesis intended for fixing the focus of an osteotomy while awaiting consolidation of the bone, which is generally substantially U-shaped, comprises a web from which issue two lateral arms having pointed ends adapted to penetrate into the bone; and the web of the agraffe comprises two parts inclined with respect to each other and forming an outwardly open obtuse angle.

The obtuse angle formed by the web of the agraffe according to the invention is chosen so that, when the agraffe is driven into the bone, for example beneath the tibial plateau, the two parts of the web inclined with respect to each other follow the shape of the outer profile of the bone as closely as possible.

According to one variation or embodiment of the invention, the two lateral arms of the agraffe are slightly divergent, such that the distance between their tips is greater than the distance between the arms where the arms join the web.

According to another variation or embodiment of the invention, each lateral arm of the agraffe presents on its inner face, i.e., the one face facing the other arm, a succession of projections of the saw-tooth type with tips directed towards the web and forming a non-return device preventing the agraffe from leaving or moving out of the bone once it has been driven into the bone.

In accordance with another embodiment of the invention, each side of each leg connected with the inner face of the leg is provided with a fin. Accordingly, each leg is provided with at least one fin and preferably two fins. The fins are located on a lateral face or side face connected with the inner face or face of each leg facing the other, where the legs of the staples pass through the hard part of the cortical bone. The primary function of the fins is to provide for increased contact surface between the staple and the cortical bone where pressure is exerted, that is, on their inner surfaces. The two sections of the osteotomy are brought together and are placed one against the other under pressure.

The contact surface between a conventional staple and the bone is too small, and there is a risk that the hole may be enlarged or the bone itself may break in another place so that the staple assembly will be broken. Because of the fins, the force which tends to separate the two sides of the osteotomy from one another is therefore better distributed along a greater surface due to the increased surface created with the use of the legs with the preferred fins. The use of the fins is separate and apart from any non-return teeth.

The "agraffe for osteosynthesis" according to the invention offers a number of advantages over heretofore known agraffes. Firstly, as its web presents or has the form of an obtuse angle, it enables the metal part of the agraffe to be applied directly on or against the bone while respecting the anatomical angle most often obtained after osteosynthesis. This increases the solidarity of the assembly and avoids excessive projection of the agraffe with respect to the bone. Furthermore, as the lateral arms of the agraffe are slightly divergent, a progressive contraction of the focus of osteotomy is obtained as the agraffe is driven into the bone. Since the teeth constituting the non-return device are provided on the inner faces of the lateral arms of the agraffe, these non-return teeth are under pressure on the bone and are particularly efficient for preventing the agraffe from coming out. Finally, the fins provided on the front faces of the lateral arms of the agraffe increase the surface of application of the forces ensuring contraction of the focus of osteosynthesis, which is particularly useful as the bone is often fragile in this anchoring zone.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 5:
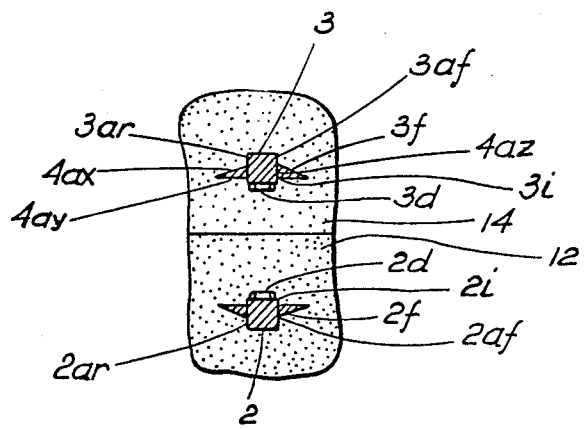
FIG. 5 is a sectional view taken on line 5—5 of FIG. 4.
Figure 6:
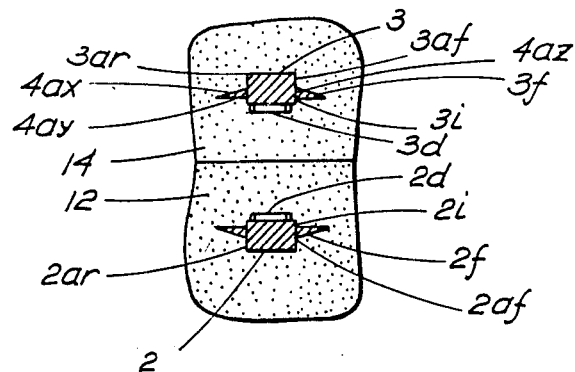
FIG. 6 is a sectional view similar to FIG. 5, but showing the legs with a rectangular cross-section.

Referring now to the drawings, the agraffe for osteosynthesis shown in the figures is generally a staple-shaped element in the form of a U-shape or inverted U and it comprises a web 1 from which issue two lateral arms 2,3. This agraffe is made of cast metal and web 1 and the two lateral arms 2,3 each present a square or rectangular cross-section. A square cross-section is shown in FIG. 5, and the agraffe with a rectangular or a quadrilateral cross-section is shown in FIG. 6.

Figure 1:
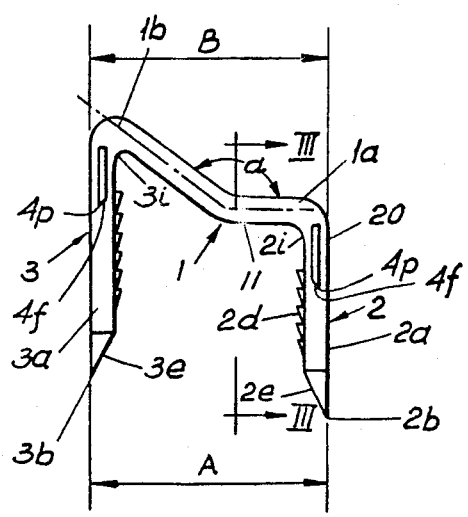
FIG. 1 is a front view of one modification of an agraffe for osteosynthesis according to the invention.

According to the invention, web or base 1 of the agraffe is constituted by two parts inclined with respect to each other and having an extent B (see FIG. 1), namely a first part 1a at whose end lateral arm 2 issues and another or second part 1b at whose end lateral arm 3 issues. The two parts 1a and 1b of the web or base thus form an outwardly open obtuse angle a therebetween, as indicated in FIG. 1. The value of this obtuse angle depends upon the application envisaged for the agraffe as will be seen hereinbelow.

Each lateral arm 2,3 includes an inner face 2i, 3i facing each other, two side faces 2a, 3a, one of which is designated as front faces 2af, 3af, and the other of which is designated as rear faces 2ar, 3ar, and outer faces 2o, 3o. Faces 2o and 3o are substantially parallel to each other, but outwardly facing.

Legs 2 and 3 terminate in tips 2b and 3b, respectively, with the long side of tip 2b being coextensive with outer face 2o and the long side of tip 3b being coextensive with outer face 3o. Tips 2b and 3b are angled so that the bevel side 2e joins inner face 2c and has a square-shaped or preferably a substantially rectangularly-shaped face, but the exact shape is dependent on the difference in length between the ends of inner face 2c and outer face 2o as well as the angle of the diagonal cut slanting from the inner face to the outer face and whether the legs are square or rectangularly-shaped in cross-section.

The spacing A between the outermost portion of tips 2b, 3b is greater than the spacing B or extent B, between the outer surfaces or faces 2o, 3o at the base of the lateral arms joining web 1.

Furthermore, in order to improve anchoring of the agraffe in the bone, each of the lateral arms 2,3 bears on its front and rear faces 2a, 3a, fins 4 projecting with respect to these front faces. These fins 4 also terminate in bevel-shaped faces 4f, and the fins have a triangular shape in cross-section (see FIG. 6) and extend longitudinally, i.e., in the direction of extension of the lateral arms 2,3 in zones adjacent the points of joining of the lateral arms 2,3 with the ends 1a, 1b of web 1, see FIGS. 1 and 4.

Bevel-shaped faces 4f extend to points 4p, and the bevel faces 4f on each fin 4 is parallel to the bevel faces 2e and 3e on the leg on which the fins are located. That is, bevel face 4f of fin 4 on leg 2 is parallel to bevel face 2e, and bevel face 4f of fin 4 on leg 3 is parallel to bevel face 3e.

It should be noted that the lateral fins 4 have an entirely different purpose from saw teeth 2d, 3d and saw teeth 2d 3d should not be confused with the lateral fins 4. Teeth 2d, 3d are located on the inner surface 2i, 3i of the legs, and surfaces 2i and 3i face each other and are not parallel to each other but slightly outwardly divergent with respect to each other when a square or rectangular cross-section, for example, is used. The spacing between the legs becomes wider as one moves from web 1 towards tips 2b, 3b to provide for better anchoring.

The fins 4 are located on at least one lateral face and preferably both lateral faces. Front faces 2af, 3af as viewed in the drawings, and rear faces 2ar and 3ar as viewed in the drawings are the lateral faces. The fins 4 are located on each lateral face where the leg of the staple passes through the hard part of the so-called cortical bone.

The fins have two functions. A first function is to increase the contact surface between the staple and the cortical bone where pressure is exerted, that is, on their inner surfaces. The second function is a result of the design of the lower points 4p of each fin 4. Each fin has its lower face bevelled so that a line joining 4p (the lowermost point) and 4b is parallel to the corresponding bevel face 2e, 3e on their respective legs 2, 3. The direction of the bevel contributes to increase the pressure between the two sides of the osteotomy by tightening one against the other, when the fins begin to penetrate into the cortical bone.

When a conventional staple is used, and the two sections of the osteotomy are brought together and placed one against the other under pressure, the contact surface between a conventional staple and the cortical bone is too small, and this can result in an enlargement of the hole or even a breaking of the bone and a tearing down of the assembly. The force which tends to separate the two sides of the osteotomy from one another is therefore better distributed along a greater surface and this is accomplished with the fins according to the present invention. Accordingly, the fins perform a totally different function than the non-return saw teeth 2d, 3d.

Figure 4:
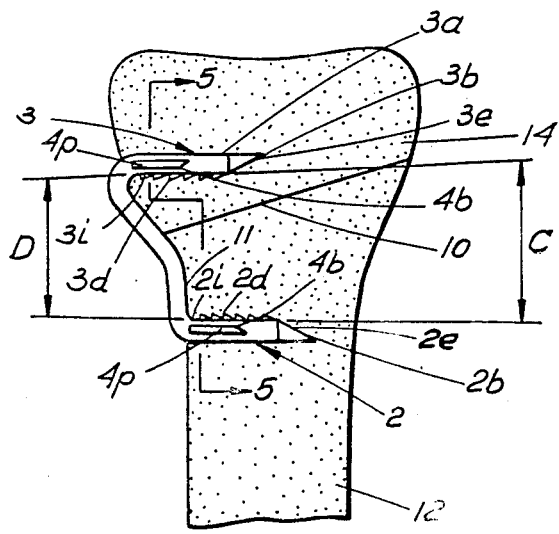
FIG. 4 is a front view of an agraffe for osteosynthesis according to the invention introduced in the upper part of a tibia, below the tibial plateau, showing fins on the side, of each of the lateral arms, connected with the inner face of each of the arms.

The lateral arms 2,3 are not parallel to each other, but, on the contrary, are slightly outwardly divergent. In other words, distance C between their tips 2b, 3b, see FIG. 4, is greater than distance D between the opposite inner faces 2i and 3i of arms 2,3, at the place where the arms join web 1. As the lateral arms 2,3 are slightly divergent, a progressive contraction of the focus of osteosynthesis is obtained as the agraffe is driven into a bone.

In order best to retain the agraffe once it has been driven into the bone, the inner faces 2i, 3i of the lateral arms 2,3 are advantageously provided with non-return devices which may be constituted by a succession of saw-teeth 2d, 3d whose tips are directed towards the undersurface 11 of web 1. As they are provided on the inner faces 2c, 3c, these saw-teeth 2d, 3d are under pressure on the bone and are particularly efficient.

As shown in FIG. 4, the agraffe for osteosynthesis according to the invention, due to the particular shape of its web 1, makes it possible to follow as best as possible the anatomical profile of the bone in the zone where this agraffe is driven in. In the case illustrated in FIG. 4, this agraffe is provided to ensure consolidation of two parts of a bone separated from each other by a saw-line below the tibial plateau.

The lateral arms 2 and 3 of the agraffe advantageously terminate in tips 2b and 3b presenting the form of inwardly facing bevels defined by faces 2e and 3e inclined inwardly starting from the ends of the tips which are coextensive and coplanar with outer faces 2o, 3o and extending to inner faces 2i and 3i, respectively, in order to facilitate penetration of the agraffe in the bone without its arms moving apart, even on a convex cortical surface.

Figure 2:
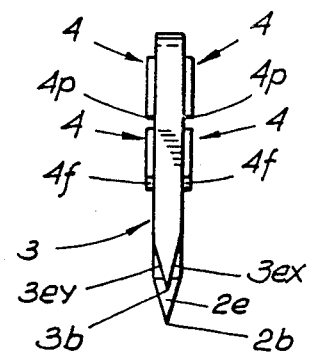
FIG. 2 is a side view of the agraffe for osteosynthesis, taken from the left in FIG. 1.
Figure 3:
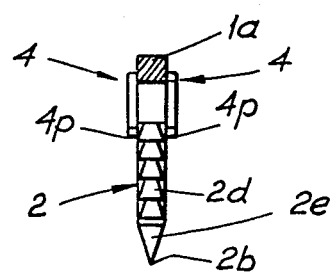
FIG. 3 is a cross-sectional view taken on line III—III of FIG. 2.

If inner faces 2i and 3i are substantially parallel to each other but have a wider spacing C than D as shown, and if bevel faces 2e and 3e are at an angle of 45° with an extension of inner faces 2i, 3i, then the bevel faces 2e and 3e would be substantially orthogonally related. The tips 2b and 3b also have side faces 2ex, 2ey and 3ex, 2ey, as best seen in FIG. 2.

The tips of each of the legs terminate in the form of a bevel defined by a face inclined outwardly away from the web 1, or can be considered to be inclined inwardly towards the web 1 starting from the ends of the pointed ends 2b, 3b in order to space apart the legs of the staple during penetration thereof into the osteotomy.

Figure 7:
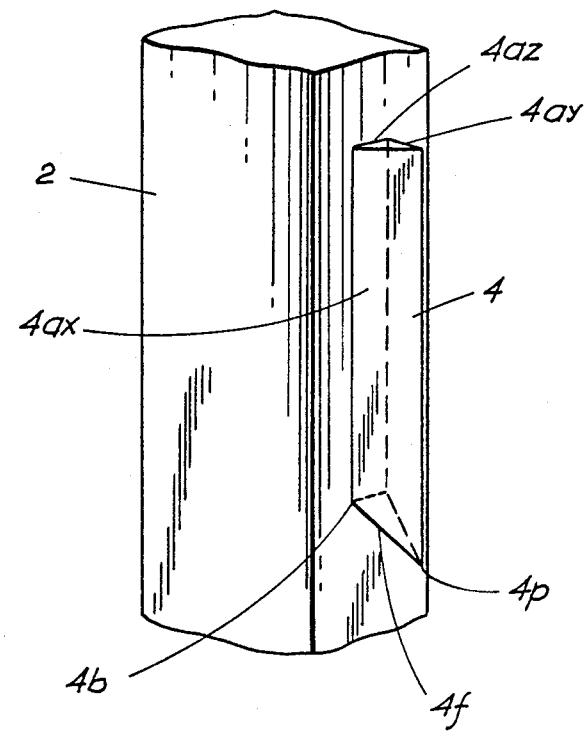
FIG. 7 is a partial perspective view of one leg of the agraffe with a fin on the side of a lateral arm, and omitting the saw teeth.

Fins 4 are generally triangularly-shaped normal to the longitudinal axis thereof in cross-section and have a trihederally-shaped, bevel-shaped tip, as best seen in FIGS. 5, 6 and 7, and include a base face 4f. Fin 4 has one of its faces positioned on front face 2af, and another fin 4 has one of its faces positioned on front face 3af; and in a preferred embodiment, fins 4 are positioned on rear faces 2ar and 3ar as well, which faces 2ar, 3ar are merely designated rear faces for purposes of explanation. The front and rear faces are the side faces connected with inner faces 2i, 3i. The fins 4 have a triangular cross-section and the lower point 4p of each fin is also beveled and has a trihederal configuration, the bevel-shaped face portion 4f being parallel to the bevel of the pointed ends of arms 2, 3.

The bevel-shaped face 4f of fin 4 on leg 2 is parallel with bevel 2e on leg 2, and in a similar manner, bevel-shaped face 4f of fin 4 which is on leg 3 is parallel with bevel 3e on leg 3. If both side faces 2af, 2ar and 3af, 3ar of the legs are provided with fins 4, then the bevels 4f of fin 4 on leg 2 are parallel with bevel 2e and bevels 4f of fin 4 on leg 3 are parallel with bevel 3e on leg 3.

Each of the fins 4 have a first side 4ax and a second side 4ay connected with a base side 4az to form the triangularly-shaped cross-section. Sides 4ax and 4ay together with the exposed surface of faces 2af, 3af and 2ar, 3ar provide for increased surface contact between the bone and the legs 2,3 of the staple. The bevel-shaped fins 4 help to maintain the spacing apart of the tips 2b, 3b of the legs so that the distance C is greater than the distance D, and the distance B as shown in FIG. 1 is less than the extent of the double-headed arrow A extending from the outer surface of the two legs facing away from each other.

In a preferred embodiment, each of the fins has a flat face substantially parallel to the inner face of each of said lateral arms.

As is well known, "osteotomy" is intended to mean the removing of a bony corner to correct the axis of a bone member, and the line 10 shows the line of joinder of 12,14 of the two sides of the tibia which faced one another and were connected to the bony corner, after the bony corner is removed and the axis is corrected so that a specially-shaped staple is necessary.

While there has been shown what is considered to be the best mode and preferred embodiments of the invention, it will be evident to those skilled in the art that various changes and modifications may be made therein without departing from the scope of the invention.

What is claimed is:

1. A generally substantially U-shaped staple for osteosynthesis intended for fixing the focus of an osteotomy while awaiting consolidation of the bone, comprising:
    a web from which issue two lateral arms having pointed ends adapted to penetrate into the bone;
    said web comprising only two parts inclined with respect to each other and forming an outwardly open obtuse angle without any step perfectly adapted to the outer profile of the bone for direct contact therewith; and
    each of said lateral arms having outwardly projecting fins, and said fins projecting solely from at least one of the front faces of each said arm and ensuring a very firm anchoring in the hard outer part of the bone.

2. The staple for osteosynthesis according to claim 1 wherein said pointed ends of each said arms terminate in tip means, each of said tip means presenting the form of bevels defined by faces inclined inwardly and upwardly towards said web starting from the ends of said pointed ends for spacing apart the legs of the staple during penetration thereof into the osteotomy.

3. The staple for osteosynthesis according to claim 1 wherein said projecting fins on each said arm are diametrically opposed to each other near the zone of joinder between said arms and said web.

4. The staple for osteosynthesis according to claim 3 wherein said projecting fins on each said arm are diametrically opposed to each other near the zone of joinder between said arms and said web.

5. The staple for osteosynthesis according to claim 1 wherein said projecting fins are generally triangularly-shaped in cross-section and diametrically opposed to each other on opposed sides of each of said lateral arms, and each of said lateral arms includes between said opposed sides saw teeth provided solely on the inner face thereof between said opposed sides.

6. The staple for osteosynthesis according to claim 1 wherein each of said fins is triangularly-shaped in cross-section normal to its longitudinal axis.

7. The staple for osteosynthesis according to claim 1 wherein each of said fins includes a lower tip remote from said web, triangularly-shaped and beveled in a direction towards said pointed ends.

8. The staple for osteosynthesis according to claim wherein said pointed ends have a flat outer side coextensive with an outer side of said lateral arms from which they extend, said pointed ends each having a beveled surface extending from said flat outer side with said bevels being inclined inwardly from a lowermost point of each of said lateral arms to an uppermost point in a direction towards said web.

9. The staple for osteosynthesis according to claim 8 wherein each of said fins includes a triangularly-shaped body and a lower tip remote from said web and beveled in a direction parallel to the bevel on its respective leg.

10. The staple for osteosynthesis according to claim 9 wherein each of said fins has a triangular cross-section and a flat face substantially parallel to the inner face of each said lateral arms.

11. A staple for osteosynthesis intended for fixing the focus of an osteotomy while awaiting consolidation of the bone, which is generally substantially U-shaped, comprising:
   a web from which issue two lateral arm means having pointed ends adapted to penetrate into the bone for increasing the pressure between two sides of the osteotomy, each of said arm means including an inner face, an outer face, a front and a rear face between said inner and outer faces;
   said web comprising solely two parts inclined with respect to each other, each of said parts being joined together at one end thereof and forming the apex of an outwardly open obtuse angle free of any step therebetween; and
   each of said lateral arm means including an arm joined to said other end of said parts and each of said arm means including at least one fin means on one of said front and said rear faces for increasing the contact surface between the staple and the bone upon exerting pressure.

12. The staple according to claim 11, wherein said lateral arms each terminate in tips, and each of said tips being bevel-shaped and defined by face inclined inwardly starting from the ends of said tips and extending in a direction towards said web for spacing apart the legs of the staple during penetration thereof into the osteotomy.

13. The staple according to claim 11, wherein said fin means includes at least one fin having a triangular cross-section projecting from at least one of said front and said rear faces of each of said arms and extending longitudinally in the direction of extension of each of said lateral arms.

14. The staple according to claim 12, wherein said fin means includes at least one fin projecting from at least one of the front and the rear faces of each of said arms and extending longitudinally in the direction of extension of said lateral arms in zones adjacent the points of joining of each of said lateral arms with ends of said web remote from said apex.

15. The staple according to claim 13, wherein said at least one fin is positioned proximate to the joint between said web and said arm.

16. The staple according to claim 14, wherein said at least one fin has a bevel-shaped tip which extends inwardly from the tip-most end towards said web and is parallel to the bevel-shaped face of the leg on which said bevel is positioned.

17. The staple according to claim 14, wherein said at least one fin includes a pointed end having a trihederal shape with a bevel face extending substantially parallel to the bevel face of said pointed ends in a direction towards said web.

18. The staple according to claim 14, wherein said at least one fin includes a pointed end having a beveled shape to form a trihederal configuration and extends from an outermost point and angled towards said web.

19. The staple according to claim 11, wherein each of said lateral arms includes saw teeth provided on the inner face thereof.

20. The staple according to claim 16, wherein each of said lateral arms includes saw teeth provided on the inner face thereof.

* * * * *